United States Patent [19]
Driscoll et al.

[11] Patent Number: 5,695,039
[45] Date of Patent: Dec. 9, 1997

[54] METHOD FOR DETERMINING A CHARACTERISTIC OF A MATERIAL

[75] Inventors: Rusty Driscoll, Leesburg; Ken R. Powell, Centreville, both of Va.

[73] Assignee: Environmental Products Corporation, Fairfax, Va.

[21] Appl. No.: 370,658

[22] Filed: Jan. 10, 1995

[51] Int. Cl.$^6$ .................................................. G07F 7/06
[52] U.S. Cl. .................... 194/212; 209/524; 209/580; 250/223 B
[58] Field of Search ................... 194/208, 209, 194/212; 209/524, 577, 580, 582, 588; 250/223 B; 356/73

[56] References Cited

U.S. PATENT DOCUMENTS

| | | | |
|---|---|---|---|
| 4,547,067 | 10/1985 | Watanabe | 250/223 B |
| 4,784,251 | 11/1988 | DeWoolfson et al. | 209/524 X |
| 5,305,090 | 4/1994 | Kowalski | 356/366 |
| 5,314,072 | 5/1994 | Frankel et al. | 209/524 X |

OTHER PUBLICATIONS

Polaroid Pamphlet, "Circular Polarizing EMI/RFI Shielding Filters", May 1993.

Primary Examiner—F. J. Bartuska
Attorney, Agent, or Firm—Finnegan, Henderson, Farabow, Garrett & Dunner L.L.P.

[57] ABSTRACT

An apparatus and method for determining a characteristic of a material, such as composition and/or color, has an electromagnetic radiation source having a first amount of circular polarization. The electromagnetic radiation from the source has the capability of passing through the material. A processor determines the characteristic of the material based on changes in the electromagnetic radiation caused by passing through the material. Changes in electromagnetic radiation include changes in rotation. Additionally, the processor may determine what, if any, electromagnetic radiation was blocked by the material and the amplitude of the electromagnetic radiation passing through the material.

14 Claims, 15 Drawing Sheets

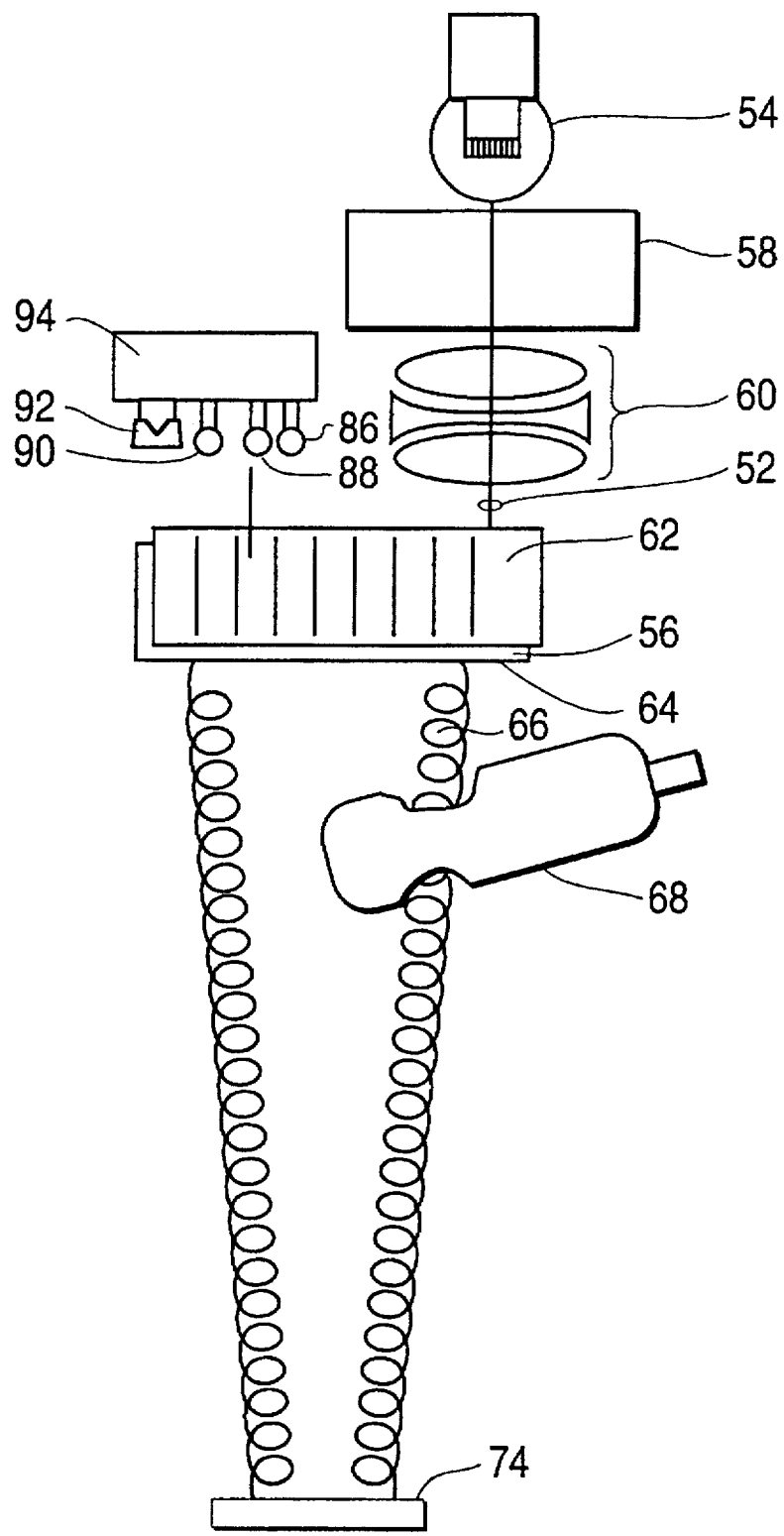

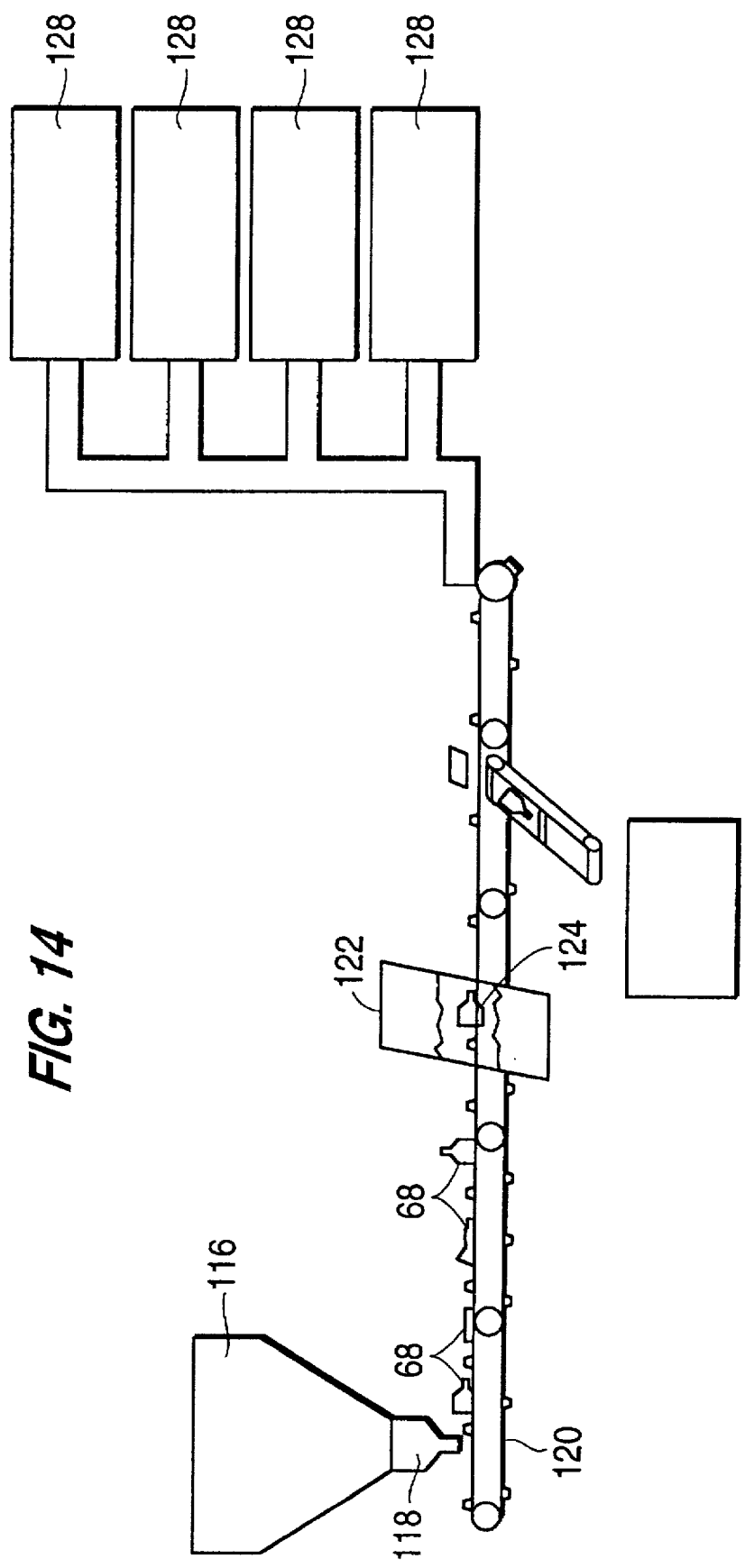

METHOD FOR DETERMINING A CHARACTERISTIC OF A MATERIAL

BACKGROUND OF THE INVENTION

1. Field of the Invention

This invention relates to determining a characteristic of a material, and, more particularly, to a method and apparatus for determining the composition and color of a material by processing circularly polarized electromagnetic radiation after having passed through the material.

2. Description of the Related Art

With the increasing emphasis in recent years on environmental protection, the recycling of used beverage containers and other similar commodities has become an important factor in the conservation effort. More specifically, the recycling of aluminum, glass and plastic containers has proven to be environmentally beneficial.

On the other hand, non-returnable containers for beverages and other goods are widely used because their cost has been less than the cost of recycling and/or cleaning reusable deposit containers and bottles. One significant effect of the widespread use of non-deposit containers has been increased litter in public places, and overflow of garbage dumps and landfills.

To combat litter and increase the amount of material that is recycled, several states have enacted mandatory "deposit laws" that require the use of containers having an added deposit cost. When the customer purchases a product in such a container, a container deposit, typically five to ten cents, is added to the purchase price. After consumption of the product, the consumer can obtain a refund of the deposit by returning the empty container, often to the retailer, for recycling. The amount of the deposit may be adjusted to create an incentive for returning the container that is greater than the inconvenience in doing so. In these states, retailers generally collect the used containers and sell them to distributors or others who pay the retailer for the scrap value of the containers plus an amount to cover the retailer's handling costs.

Since the high labor cost of processing recycled material often makes recycling uneconomic, especially for retailers, various automatic machines that accept material for recycling and issue deposit refunds have been proposed. These machines relieve the burdens on the grocery industry and those who must collect the containers, pay the refunds, and store the returned commodities. For example, Applicant's Assignee is the owner of U.S. Pat. Nos. 4,324,325; 4,345,679; 4,440,284; 4,469,212; 4,492,295; 4,573,641; 4,579,216; 4,784,251; 5,226,519; and 5,355,987. All of these patents relate to machines and systems for automated redemption of beverage containers.

Another approach to improving the economics of recycling is to increase the scrap value of the recycled material. One method for increasing the scrap value is to segregate the return material into groups whose scrap price inherently is higher than the scrap price of unsegregated material. Separation of scrap by composition (for example, glass, aluminum, paper, and plastic) or by color (for example, clear glass and green glass) greatly increases the value of the scrap material. Separation of plastic scrap further according to chemical makeup also is desirable with vinyl based container scrap being excluded from mixture with high density polyethylene, polypropylene, and polyethylene terephthalate (PET) container scrap.

In the past, segregation of returned containers has been labor-intensive, so that the labor to perform the sorting can sometimes cost more than the increase in resale value of the segregated material. It would be highly desirable to provide a device that can perform the segregation of materials into such groups quickly and inexpensively, so that the cost of the sorting process is less than that of the enhancement in value obtained through the sorting. It would be particularly desirable to provide such a sorting device that could be utilized at the point of return of the recycled material, because the person charged with recycling (typically the retailer) would enjoy the enhancement and profit arising from its use. It is expected that such an approach would greatly increase industry support for recycling various materials.

There are few available apparatuses and processes for grading and sorting containers by a material's construction and color. Apparatus have been used wherein linearly polarized light of at least two known wavelengths is passed through a container. Portions of the transmitted beam are analyzed by parallel and cross polarizers, the intensities of the analyzed beams are measured, and the sum and difference of the analyzed beams are determined to yield information concerning the color and composition of the container. While the aforementioned apparatus proved useful in some applications, it requires a container support to hold the container in a specific orientation to the linearly polarized light in order to assure that the polarized light actually will pass through the container to provide useful data. While the light passes through the container regardless of orientation, useful data is lost as the orientation degrades.

Apparatuses and methods for grading and sorting containers by material, composition, and color should meet the requirements discussed previously, and also be operable with containers that are less than ideal, such as those which have been crushed, damaged in some way, are dirty, or have labels. Moreover, a precise orientation of the container should not be required for determining a characteristic of the material.

More generally, it is desirable to provide a method and apparatus for determining a characteristic of a material by using electromagnetic radiation having circular polarization and processing the radiation after passing through the material to determine the characteristic of the material based on a change in the electromagnetic radiation. It is contemplated that such technology has many applications for determining a characteristic of a material or in obtaining additional information on various materials for many different industries, as well as the recycling industry.

SUMMARY OF THE INVENTION

Accordingly, it is the object of the present invention to determine a characteristic of a material, such as the composition and/or color, and to overcome the deficiencies of the devices discussed above.

Additional objects and advantages of the invention will be set forth in the description which follows, and in part will be obvious from the description, or may be learned by practice of the invention. The objects and advantages of the invention will be realized and attained by means of the elements and combinations particularly pointed to in the appended claims.

The present invention provides a method and apparatus for automatically sorting materials. Most commonly, in the recycling industry the materials being sorted are containers for beverages, consumable products, or the like, and among that group, most commonly beverage bottles. For the purpose of simplicity but not to limit the scope of the present invention, materials being sorted in accordance with the present invention when referencing the recycling industry will be referred to simply as containers. Within the recycling industry, materials such as containers that traditionally have been sorted, have had the requirement of being transparent or partially transparent to visible light and held with the axis of the container at a specific orientation to the light beam so as to be sorted between optically active and optically inactive materials, and as between different colors. The term "optically active" refers to materials that cause the rotation of polarized light.

The present invention provides an inexpensive, reliable method and apparatus for sorting containers regardless of material, orientation of the material to the directed radiation, level of transparency to visible light, or color. The sorting is accomplished rapidly, normally as fast as a consumer places the containers into the apparatus. Alternatively, a conveyor system may be used to sort the containers in bulk. Once sorted, the containers are conveyed to bins or storage areas for containers of the same color and composition. While the primary application of the preferred embodiment of the invention is utilized to sort between various containers, it should be understood that within various industries, the application may be directed simply to identifying a specific material or purity of material alone and that the embodiment directed to sorting materials does not limit the scope of the present invention.

To achieve the objects and in accordance with the purposes of the invention, as embodied and broadly described herein, the method of the invention comprises the steps of directing an electromagnetic radiation having a first amount of circular polarization toward a material and processing the electromagnetic radiation after passing through the material to determine the characteristic of the material based on a change in the electromagnetic radiation. The step of processing includes determining changes in rotation, as well as any electromagnetic radiation being blocked by the material and the amplitude of the electromagnetic radiation passing through the material. The step of processing may be used to determine the composition or color of the material.

Preferably, the material is introduced to a radiating area prior to the step of directing. The radiating area may be contained within a reverse vending machine including a housing, a mechanism in the housing for receiving a container of a given material, and a storage portion configured to receive the container.

The method in accordance with the present invention may also include the step of receiving the electromagnetic radiation having passed through the material and having a second amount of circular polarization, and removing the first amount of circular polarization from the electromagnetic radiation having the second amount of circular polarization prior to the step of processing. Additionally, the method may include the step of reversing the direction of rotation of the electromagnetic radiation having the second amount of circular polarization prior to the step of removing.

The method in accordance with the present invention may further include producing electromagnetic radiation having circular polarization prior to the step of directing. The step of producing includes radiating an electromagnetic radiation and circularly polarizing the electromagnetic radiation with a direction of rotation. Preferably, the steps of producing includes illuminating with a polychromatic light source and passing the electromagnetic radiation from the light source through a first circular polarizing filter. The step of removing includes passing the electromagnetic radiation through at least one second circular polarizing filter. Moreover, in an alternative embodiment, a single polarizing filter may be used in both the step of producing and the step of removing.

The invention also includes an apparatus for determining a characteristic of a material comprising an electromagnetic radiation source having a first amount of circular polarization, the electromagnetic radiation being capable of passing through the material, and a processor to determine the characteristic of the material based on changes in the electromagnetic radiation caused by passing through the material. The apparatus may be contained within a reverse vending machine comprising a housing, a mechanism in the housing for receiving a container of a given material, and a storage portion configured to receive the container. The electromagnetic radiation source preferably includes a polychromatic light source and a first circular polarizing filter. The processor preferably includes a plurality of photoreceivers for generating signals based on receiving the electromagnetic radiation having passed through the container and a computer algorithm for collecting signals from the receivers and comparing them to a table having values representing known material characteristics.

Another embodiment includes a material sorting apparatus including an assembly for determining a characteristic of a material. The material sorting apparatus further includes an area for receiving containers and a conveyor for singulating the containers for delivery to the assembly for determining the characteristic of the material. After the composition and/or color of the container has been determined, undesirable containers are rejected from the container string, and acceptable containers are sorted into various storage bins configured to receive the containers.

Thus, the method and apparatus of the invention provides an approach to accomplish the determination of a characteristic of a material, and more particularly the sorting of containers without the necessity of human labor or intervention. The approach is operable in conjunction with a reverse vending machine or the like, so that the customer is rewarded for recycling the material with a cash refund of coupons that may be redeemed. Other features and advantages of the present invention will be apparent from the following more detailed description of the invention, taken in conjunction with the accompanying drawings, which illustrate, by way of example, the principle of the invention.

It is understood that both the foregoing general description and the following detailed description are exemplary and explanatory only, and are not restrictive of the invention as claimed.

BRIEF DESCRIPTION OF THE DRAWINGS

The accompanying drawings, which are incorporated in and constitute a part of the specification illustrate a preferred embodiment of the invention. Together with the description, they serve to explain the objects, advantages and principles of the invention. In the drawings:

FIG. 3A is a schematic drawing of an apparatus in accordance with a third embodiment of the present invention for determining a characteristic of a material;

FIG. 14 is a schematic drawing of an apparatus in accordance with a fifth embodiment of the present invention for determining a characteristic of a material.

DESCRIPTION OF THE PREFERRED EMBODIMENTS

Reference will now be made in detail to the present preferred embodiments of the invention, as illustrated in the accompanying drawings.

Figure 1:
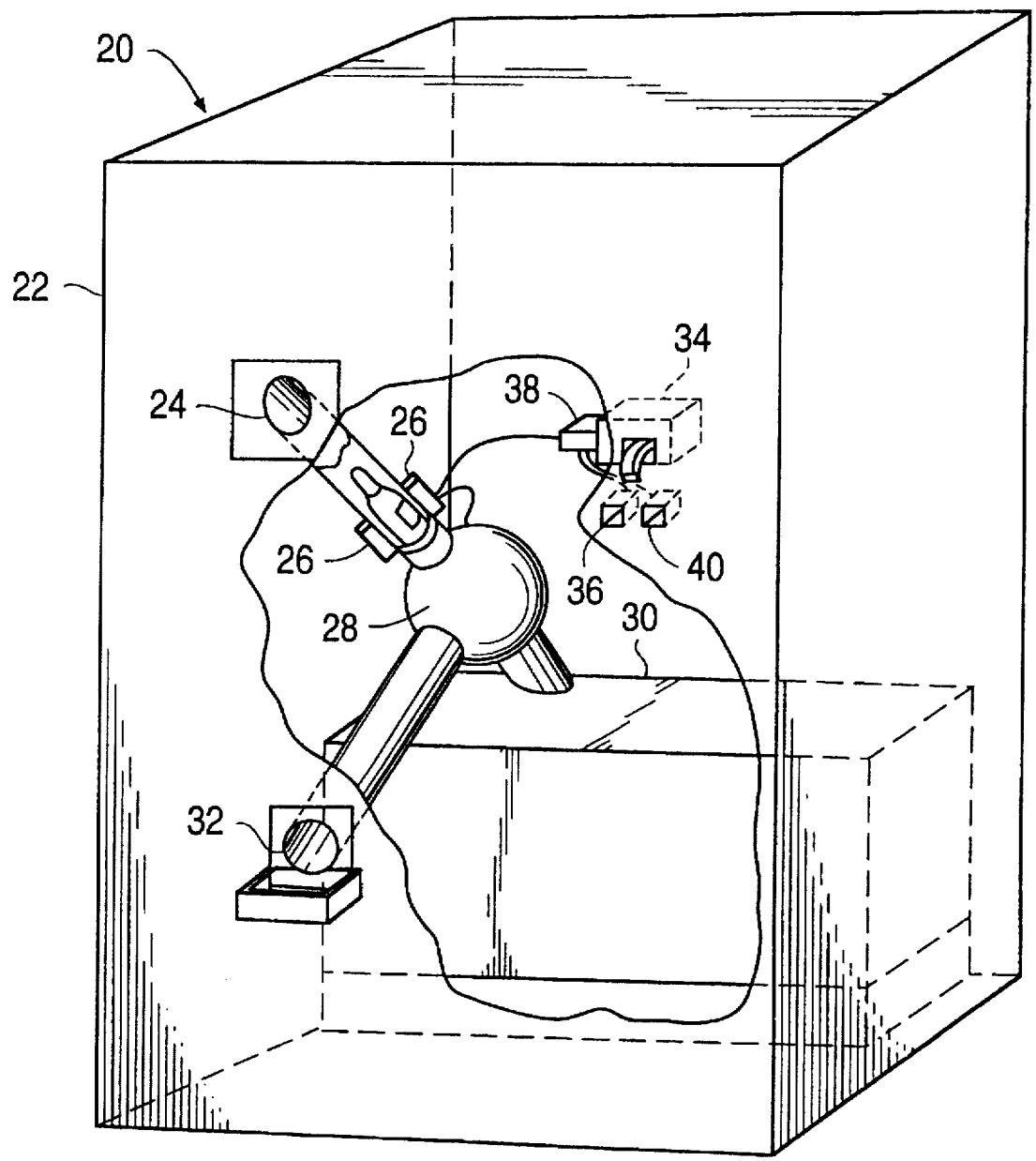
FIG. 1 is a perspective view of a recycling apparatus capable of employing the method and apparatus of the invention, with interior portions illustrated in cut-away view for clarity.

As broadly embodied in FIG. 1, the present invention may be used in recycling apparatus 20 for receiving and sorting containers, for example a reverse vending machine. Apparatus 20 includes housing 22 having receiving receptacle 24 therein, for receiving empty containers inserted therein by a customer. Containers received in receptacle 24 pass through sorting station 26, the operation of which is described in detail below. Sorted containers leave sorting station 26 and travel through sorting gate 28, and into one of a plurality of bins or storage portions 30 for storage and/or densification, or to return chute 32 that returns unacceptable containers to the customer. Sorting gate 28 directs the container to a proper bin for storage or densification, such as, for example, storage portion 30, or return chute 32 under command of sorting station 26.

Reward dispenser 34 delivers a reward to the customer for returning the containers, typically in the form of cash or coupons redeemable for goods, under control of reward total accumulator 38. Reward dispenser 34 typically permits the customer to choose whether the reward is to be in the form of cash or other type of available reward. On the face of apparatus 20 is start button 36 that signals apparatus 20 that a particular customer is commencing the return of a series of one or more containers. Pressing start button 36 causes rewards accumulator 38 to be set to zero. Each acceptable container sensed by sorting apparatus 26 causes reward accumulator 38 to be incremeted by a proper amount, thereby keeping a running total of the reward due the customer. When the customer has deposited all the containers to be returned, end button 40 is depressed to signal reward accumulator 38 that the return process is completed. Reward accumulator 38 then provides an indication of the total reward to the customer. This indication may be purely visual, such as through an electronic display, or may be tangible, such as through a printed receipt. The structure of the recycling apparatus is known to those skilled in the art, except for the structure and operation of the sorting apparatus or station 26, and is described, for example, in U.S. Pat. No. 5,355,987 and U.S. patent application Ser. No. 08/321,864, filed Oct. 17, 1994, now U.S. Pat. No. 5,630,493 the disclosures of which are incorporated herein by reference.

As disclosed in U.S. Pat. No. 4,784,251, owned by Applicants' assignee, the description of which is incorporated herein by reference, a laser scanner exists for determining the color and composition of a material by reading a barcode. The laser scanner includes a low power laser emitter and a laser reader. A barcode is a specific arrangement of bars or elements that contains information such as an identification of the product to which it is affixed, as well as the color and/or material of which the container is made. Thus, by reading the barcode, the material and color of the container can be determined. In a conventional apparatus, if the barcode or label containing a barcode deliberately or inadvertently are placed on the wrong container, an erroneous determination of that container's color and/or composition may result. Accordingly, the present method and apparatus provides a way to verify that the information included in the barcode is accurate. This is particularly useful where, in addition to sorting containers by color and composition, it is desirable to keep a record of the manufacturer and/or distributor of the containers. It should be understood, however, that the present invention also is useful in a system where the barcode is not read at all.

Figure 2A:
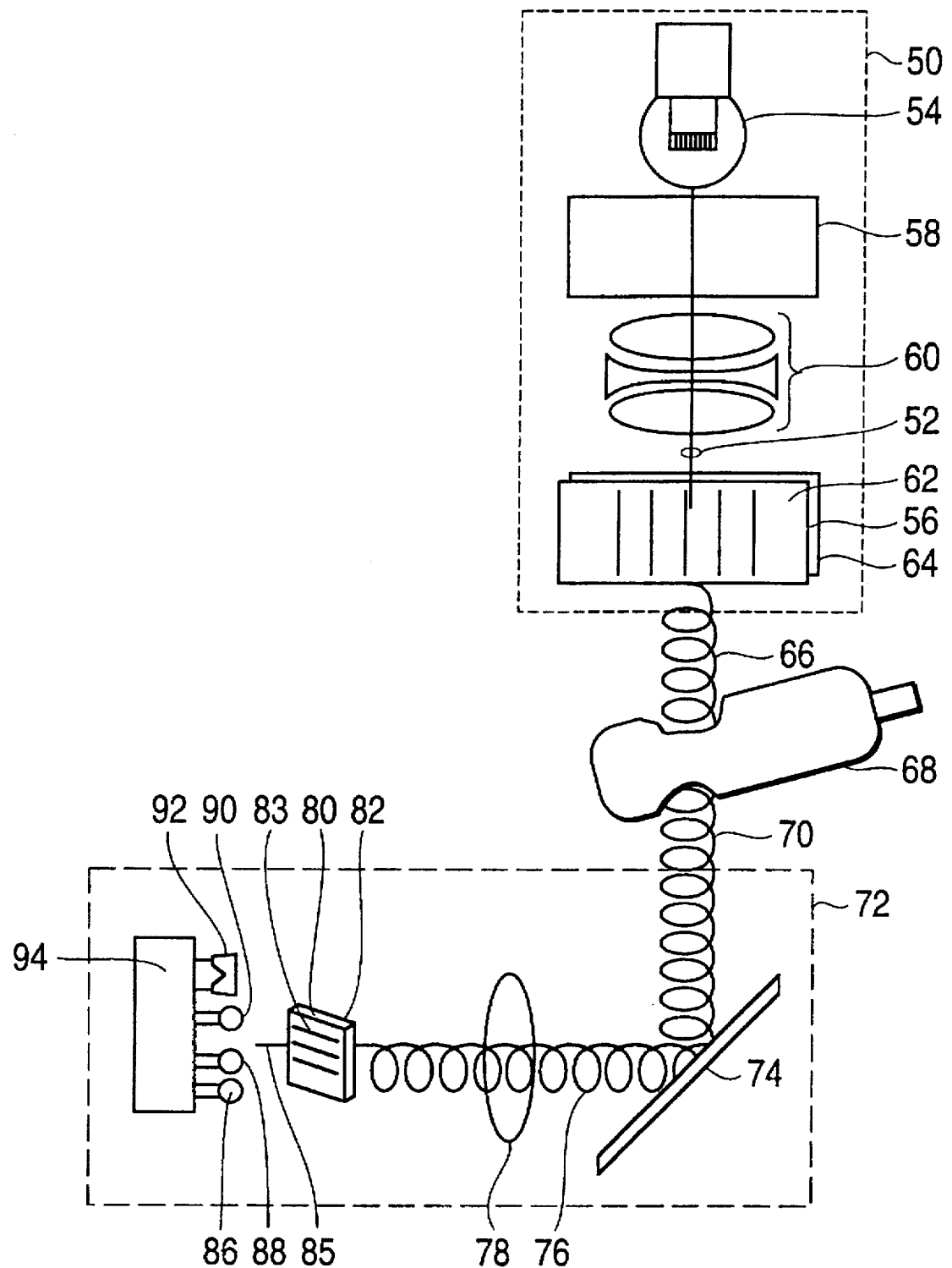
FIG. 2A is a schematic drawing of an apparatus in accordance with a first embodiment of the present invention for determining a characteristic of a material.
Figure 2B:
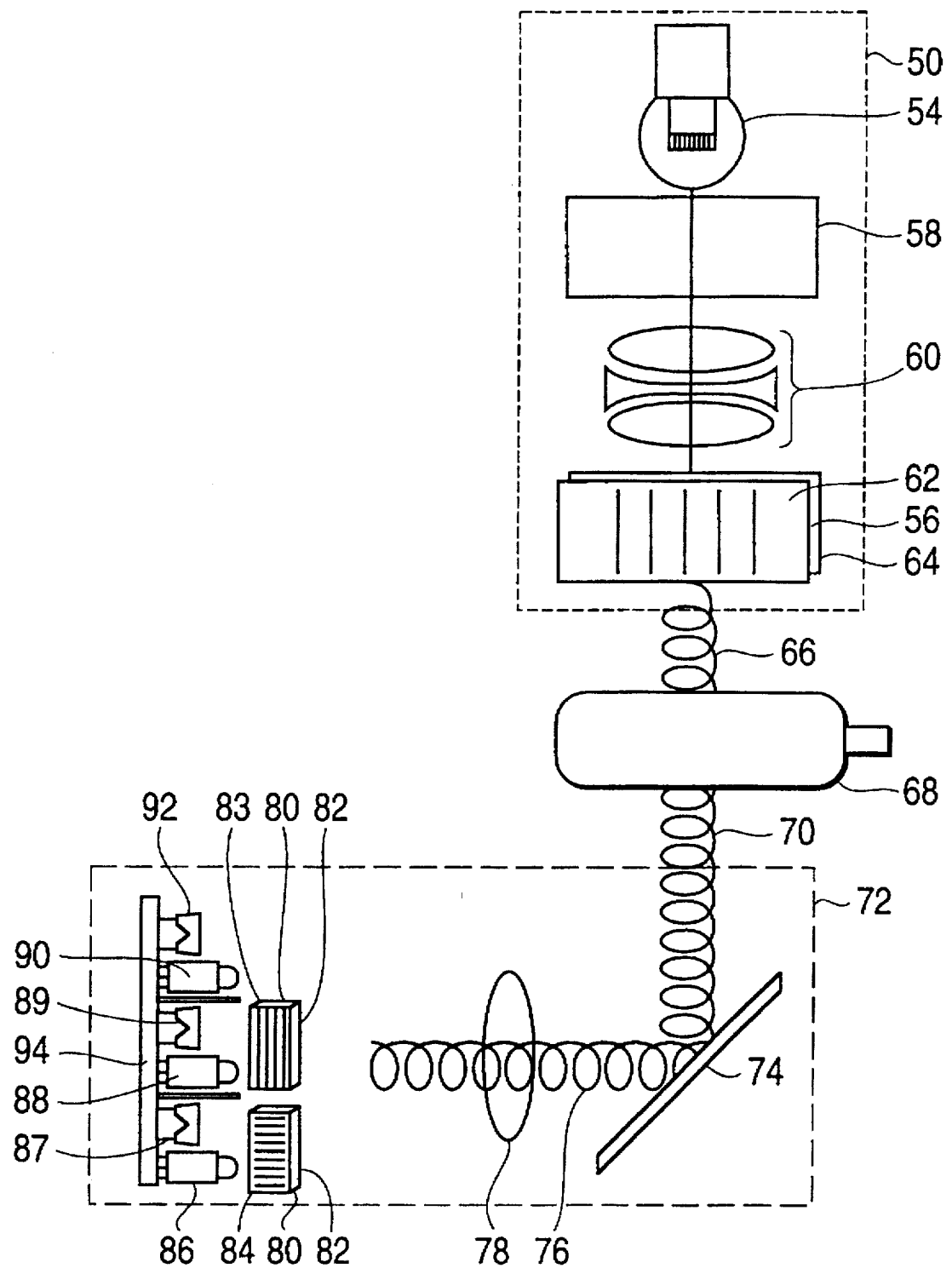
FIG. 2B is a schematic drawing of an apparatus in accordance with a second embodiment of the present invention for determining a characteristic of a material.

In accordance with the present invention, an apparatus for determining a characteristic of a material is shown schematically in FIGS. 2A and 2B. The apparatus includes an electromagnetic radiation source having a first amount of circular polarization for directing electromagnetic radiation along an axis through a material, such as a container, at least a portion of the directed electromagnetic radiation having the capacity to pass through the material. As broadly embodied herein, electromagnetic radiation source 50, which directs electromagnetic radiation along axis 52 is provided, shown in FIGS. 2A and 2B enclosed within the box formed by dashed lines. Electromagnetic radiation source 50 preferably includes polychromatic light source 54 and first circular polarizing filter 56. Filter 58 and a lens or series of lenses 60 may be used between polychromatic light source 54 and first circular polarizing filter 56 to block out certain excess amounts of unwanted electromagnetic radiation, such as infrared waves, and to focus light source 54 toward first circular polarization filter 56, respectively.

The preferred circular polarizing filter 56 includes linear polarizer 62 having a phase orientation and quarter wave retarder 64. Polaroid Corporation makes a variety of acceptable circular polarizers, especially for use in flat-panel displays to reduce common glare problems, such as those experienced when sunlight or fluorescent light strikes a CRT screen. A preferred circular polarizer 56 for use in circularly polarizing the electromagnetic radiation from light source 50 for use in recycling apparatus 20 includes a Polaroid-type H circular polarizer. This circular polarizer consists of a type H linear polarizing filter and a quarter wave retarder element in slow and fast axis at 45° to the axis of the polarizing filter.

Preferably, the circularly polarized light having a first amount of circular polarization and represented in FIGS. 2A and 2B by first spiraled axis 66 is directed toward container 68. The electromagnetic radiation or light from polychromatic light source 54 has a second amount of circular polarization having a selected direction of rotation upon exiting the container. The second amount of circular polarization is represented by second spiral axis 70.

All materials are translucent to certain waves of a given wavelength. Electromagnetic radiation takes many forms including a single wavelength source, polychromatic light source, and infrared, gamma, and x-ray sources, which can be directed toward a given material. Single or multiple waves of the same or different wavelengths may pass through a given material. Interaction between the electromagnetic radiation and the material causes a change in the polarization of the electromagnetic radiation as it interacts with the atoms or the molecular chains of the material. Photons may be shifted or no longer quite circular in their polarization. Reference to any particular electromagnetic radiation source or range of wavelengths is not meant to be limiting upon the invention contained herein. It is contemplated that the electromagnetic radiation source or sources may vary according to the demands of a user and the particular materials upon which one desires to make a determination of its characteristics.

The preferred polychromatic light source 54 includes a halogen light, which can provide very broad, ultraviolet through infrared electromagnetic radiation. While the preferred source is a polychromatic light source, it is contemplated as well that all types of electromagnetic radiation including radio waves, transmission waves, and sound waves may be circularly polarized and capable of passing through material. For example, a radio transmitter may be built to transmit a circularly polarized wavelength capable of passing through a material.

Any containable material including gas, solid, or liquid or any combination thereof, may be processed or analyzed using the present invention. The electromagnetic radiation source need only be modified to ensure that some portion of the electromagnetic radiation passes through the material. By way of example, if recycling apparatus 20 was required to sort various plastic containers including those being black in color, which would block visible light entirely, then infrared could be included with the electromagnetic radiation, thereby providing radiation that can pass through the container and hence be processed.

In accordance with the invention, the apparatus further includes a processor to determine the characteristic of the material based on changes in the electromagnetic radiation caused by passing through the material. As broadly embodied herein, processor 72, which determines the characteristics of the material based on changes in the electromagnetic radiation caused by passing through the material is provided, shown in FIGS. 2A and 2B enclosed within the box formed by dashed lines. After passing through container 68, the electromagnetic radiation having a second amount of circular polarization is reflected by a mirror 74, thereby reversing the direction of rotation of the circularly polarized electromagnetic radiation as represented by third spiral axis 76. A lens 78 may be used to focus the electromagnetic radiation on second circular polarizing filter 80.

In the embodiments of FIGS. 2A and 2B, the electromagnetic radiation passes through circular polarizing filter 80 in a direction that first eliminates an amount of circular polarization equal to that introduced by first circular polarizing filter 56 from the electromagnetic radiation having a second amount of circular polarization. This is accomplished by passing the electromagnetic radiation having a second amount of circular polarization with a reversed direction of rotation through quarter wave retarder 82, then through linear polarizer 84 of second circular polarizing filter 80. The quarter wave retarders 82 of the first and second circular polarizing filters 56, 80 preferably are the same. Through this arrangement, quarter wave retarder 82 of second circular polarizing filter 80 removes the initial circular nature of the electromagnetic radiation caused by first circular polarizing filter 56.

In the embodiment of FIG. 2A, linear polarizer 84 of second circular polarizing filter 80 is oriented 90° out of phase to that of first circular polarizing filter 56. This arrangement blocks light, which is oriented in the direction linearly polarized by linear polarizer 62 of first circular polarizing filter 56, from passing through second circular polarizing filter 80. Hence, the only electromagnetic radiation passing out of second circular polarizing filter 80 is that which has been changed due to its interaction with the container 68. The electromagnetic energy passing out of second circular polarizing filter 80 along axis 85 represents the electromagnetic radiation changed by passing through the material. Preferably, photoreceivers 86, 88 are oriented with respect to second circular polarizing filter 80 to receive the electromagnetic radiation exiting filter 80.

In the preferred embodiment of FIG. 2B, second circular polarizing filter 80 is divided into two portions. The second circular polarizing filter 80, as with the embodiment of FIG. 2A, has a quarter wave retarder 82 and a linear polarizer. The two portions of the second circular polarizing filter 80 are distinguished from one another in that one portion has linear polarizer 83 oriented parallel with the linear polarizer 62 of first circular polarizing filter 56. As with the embodiment of FIG. 2A, linear polarizer 84 of second circular polarizer filter 80 is oriented 90° out of phase to that of first circular polarizing filter 56. In the preferred embodiment shown in FIG. 2B, two additional photoreceivers 87, 89 are situated adjacent to photoreceivers 86 and 88. Photoreceivers 87, 89 serve as an intensity sensor to determine the strength of the color shift detected by photoreceivers 86, 88 and additionally validate the reading.

The primary advantage to using a circular polarizer is that it eliminates the container orientation requirement. Additionally, the circular polarizer adds the use of color in determining the material as well as the amplitude information. Light passes through the material regardless of the type of polarization. However, for linear polarized light to provide useful data, the container must be oriented with the long axis of the container at 45° to the light's axis of polarity.

In the embodiments of FIGS. 2A and 2B there is a photoreceiver 90, which is a color sensor, and a photoreceiver 92, which is an intensity sensor. Both receive electromagnetic radiation having passed through the material without having second circular polarizing filter 80 along the path to remove any of the electromagnetic radiation. This results in a color measurement and an intensity measurement. Using log ratio circuitry to convert the signals from photoreceivers 86, 88, 90, 92, voltage values that are representative of the average wavelength transmitted through the material are determined. The intensity measurement is obtained by converting the output from photoreceiver 92 to a logarithmic voltage proportional to the illumination intensity. By collecting these voltage values, a determination may be made as to the composition of the material. This may be done using a lookup table. All data is analyzed using the no-sample material condition as a base reference.

Electromagnetic radiation having multiple wavelengths is preferred in order to make comparisons between how the material affected the electromagnetic radiation of one wavelength versus that of another wavelength. The use of first and second circular polarizing filters 56, 80 provides the capability to transmit and then block wavelengths of the initially directed electromagnetic radiation from both photoreceivers 86, 88, thereby permitting the collection of the information pertaining to color and intensity for both wavelengths that transmit through both sides of second circular polarizing filter 80. However, a single wavelength may be used for certain applications where a material affects that wavelength in a known manner, which identifies the material. The use of a single wavelength eliminates the requirements for a color detector and allows for an amplitude-based decision by using a photodiode. The single wavelength application requires tight controls on the material being detected.

The color value from photoreceivers 86, 88, 90 indicates how the structure of the material affected the various wavelengths of circularly polarized electromagnetic radiation. As circularly polarized electromagnetic radiation passes through the material, it is affected by the structure of the material. This effect is wavelength dependent and produces a color shift in the electromagnetic radiation that passes through second circular polarizing filters 80, 81. Photoreceivers 86, 88 each have an associated second circular polarizer, which preferably have their respective linear polarizer portions 90° out of phase with one another. This orientation difference permits specific effects of some materials that shift the light to a polarized state to be identified. This shift can be further correlated by using the color value of photoreceiver 90 as the indicator for the average color of electromagnetic radiation or light passing through the container. Effectively, this is used to subtract out the color change effects due to dyes in the material. The remaining color change in color value can then be attributed to the affect that the material had on the circularly polarized electromagnetic radiation.

In the embodiment of FIG. 2A, values from photoreceiver 92 are used to validate the color readings. In the preferred embodiment of FIG. 2B, values from photoreceivers 87, 89, 92 are used to validate the color readings. If the electromagnetic radiation available for analysis drops below a valid reading threshold, then there is not enough electromagnetic radiation to make a reliable color measurement. This allows the processor to avoid having false readings due to low light conditions. The intensity values also allow standard transmission values to be set for each material to be analyzed. For example, if a material exhibits color change values and indicates the material is polystyrene or high density polyethylene, the intensity value could be used to decide which of the materials is being tested.

Photoreceivers 86, 88, 90 detect the color of the container depending upon the relative magnitudes of the received signals. Photoreceivers 86, 88, 90, in accordance with the present invention, may be embodied, for example, and connected to microprocessor 94. Further details of the electrical circuitry for color detection is described below in reference to FIG. 4.

As embodied herein and shown in FIGS. 2A and 2B, photoreceiver 92 for intensity detection is provided, to which electromagnetic radiation is directed. Photoreceiver 92 is connected to microprocessor 94. The signal from photoreceiver 92 is processed in a manner described below in reference to FIG. 5 to determine if there is sufficient light to obtain an accurate reading. If, for example, in a recycling apparatus 20, container 68 blocks a large percentage of the electromagnetic radiation from light source 54, it may be necessary to reject container 68 to return chute 32.

Figure 3B:
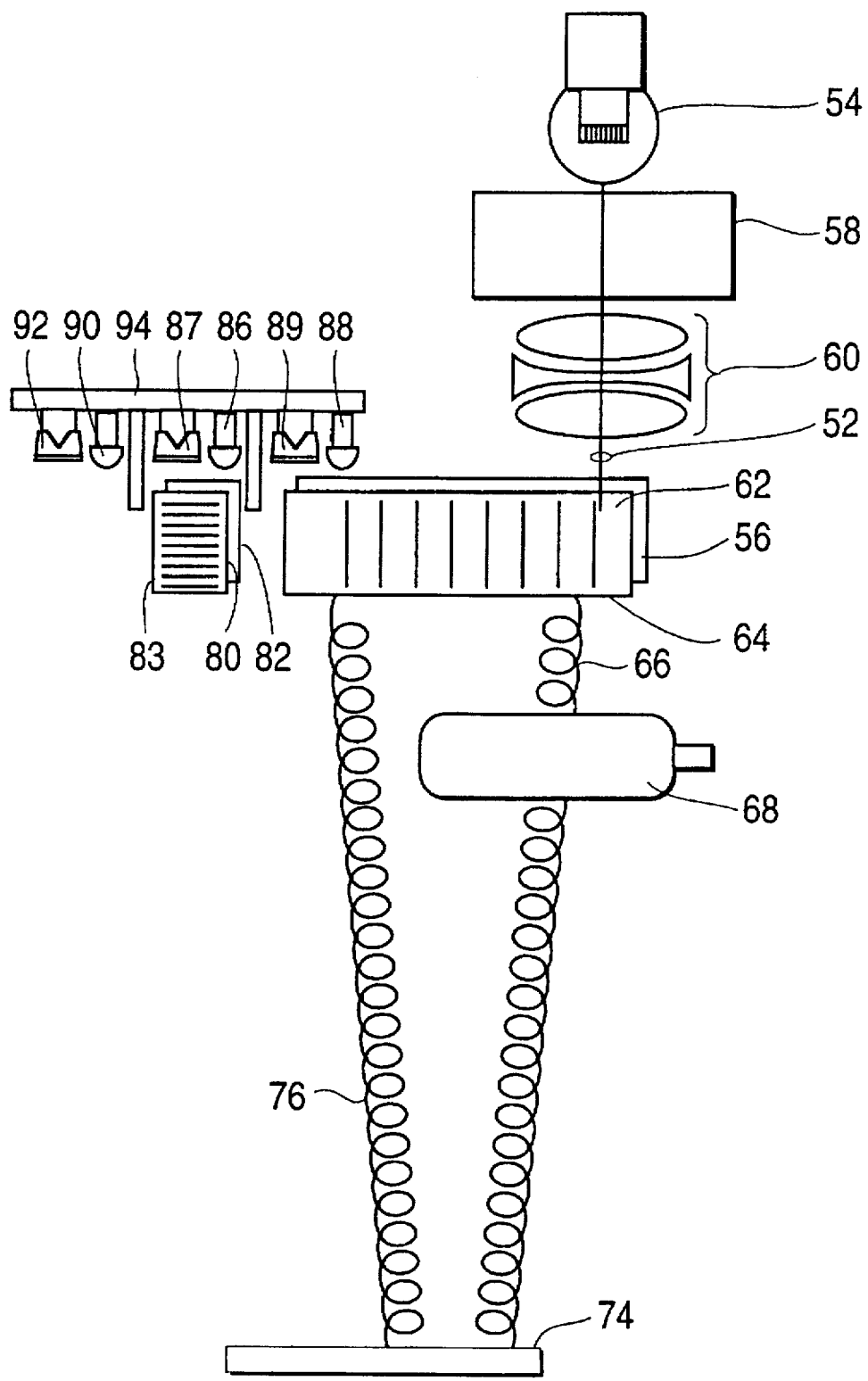
FIG. 3B is a schematic drawing of an apparatus in accordance with a fourth embodiment of the present invention for determining a characteristic of a material.

Other embodiments of the present invention are shown in FIGS. 3A and 3B. The description of the elements of the embodiment of the present invention shown in FIGS. 3A and 3B are the same as for the corresponding elements of the embodiment shown in FIGS. 2A and 2B, which bear the same reference numerals.

In the embodiments of the invention shown in FIGS. 3A and 3B, electromagnetic radiation from polychromatic light source 54 passes through first circular polarizing filter 56, then through container 68 as in the embodiments shown in FIGS. 2A and 2B. However, upon hitting mirror 74 to reverse the direction of rotation of the electromagnetic radiation now having the second amount of circular polarization, the electromagnetic radiation is directed back toward first circular polarizing filter 56 so as to pass through filter 56 in a direction opposite that in which the polychromatic light source 54 initially directed the electromagnetic radiation. The effect of this is that a single circular polarizing filter may be used for both producing the electromagnetic energy having circular polarization and for removing the circular polarization from the electromagnetic energy having a second amount of circular polarization after passing through the material.

FIG. 3A shows processor 72 including photoreceivers 86, 88, 90, 92 as contained in the embodiment shown in FIG. 2A. In the alternative embodiment of FIG. 3A, linear polarizer 62 of first circular polarizing filter 56 does not provide a 90° difference in phase orientation as the electromagnetic radiation passes in opposite directions. Depending on the application to which the apparatus and method are directed, this difference may have little effect in the quality of the determination. Moreover, the 90° difference in phase orientation can be provided either by mechanically or electrically rotating the electromagnetic radiation or filter 56. In the embodiment of FIG. 3B, as with FIG. 2B, a portion of the circular polarizing filter is oriented 90° from that of the adjacent portion to provide different data to the photoreceivers 86, 88. The embodiment illustrated in FIGS. 3A and 3B have the advantage of a more compact design by allowing the electronics to exist in a single place.

While both embodiments of the present invention include removing the first amount of circular polarization from the electromagnetic energy having a second amount of circular polarization in order to analyze the remaining electromagnetic radiation and hence the change in the electromagnetic radiation caused by passing through the material, this is not contemplated to be limiting upon the scope of the invention. The processor 72 may determine the change caused by the material by measuring the electromagnetic radiation having a second amount of circular polarization and doing an internal or electronic comparison to the electromagnetic radiation having a first amount of circular polarization which is directed toward the material.

Figure 4:
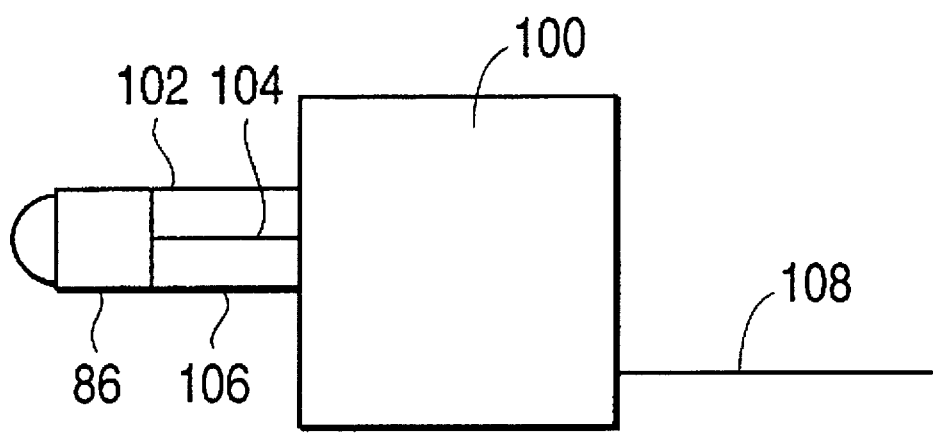
FIG. 4 is an embodiment of a color detector electronic circuit.
Figure 5:
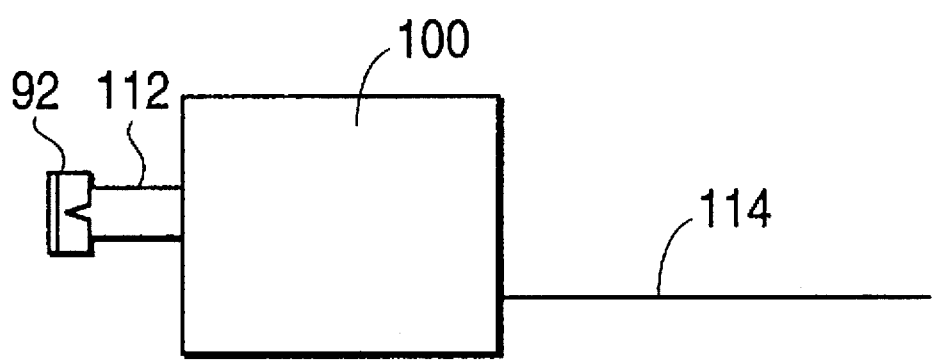
FIG. 5 is an embodiment of an intensity detector electronic circuit.

By way of example and not limitation, one possible set of electronics for the embodiments of FIGS. 2A, 2B, 3A and 3B are shown in FIGS. 4 and 5. In one embodiment, the electronic circuit shown in FIG. 4 for a color detector operates in the following manner. A color sensor is connected into log ratio amplifier 100 along connection points 102, 104 and 106. Preferably, connection point 102 carries a first current; connection point 104 serves as a ground; and connection point 106 carries a second current. The log ratio amplifier 100 has an output 108. The output 108 provides a voltage out of the log ratio amplifier 100 based on the following formula:

$$V_{OUT} = k * LOG(I_1/I_2),$$

where k is a gain multiplier constant, $I_1$ is the current along connection point 102, and $I_2$ is the current along connection point 106.

The output is proportional to the average color value.

In one embodiment, the electronic circuit shown in FIG. 5 for an intensity detector operates in the following manner. A photodiode is connected to a log amplifier 110 via connecting points 112 which carry current. The log amplifier 110 has an output 114 which produces a voltage out based on the formula $V_{OUT} = k * LOG(I1)$, where k is a gain multiplier constant and $I_1$ is the current from the photodiode.

In experiments utilizing the preferred embodiment described above, PET, vinyl, glass, high-density polyethylene, low-density polyethylene, polypropylene, and polystyrene have been successfully identified according to their composition and color.

Figure 6:
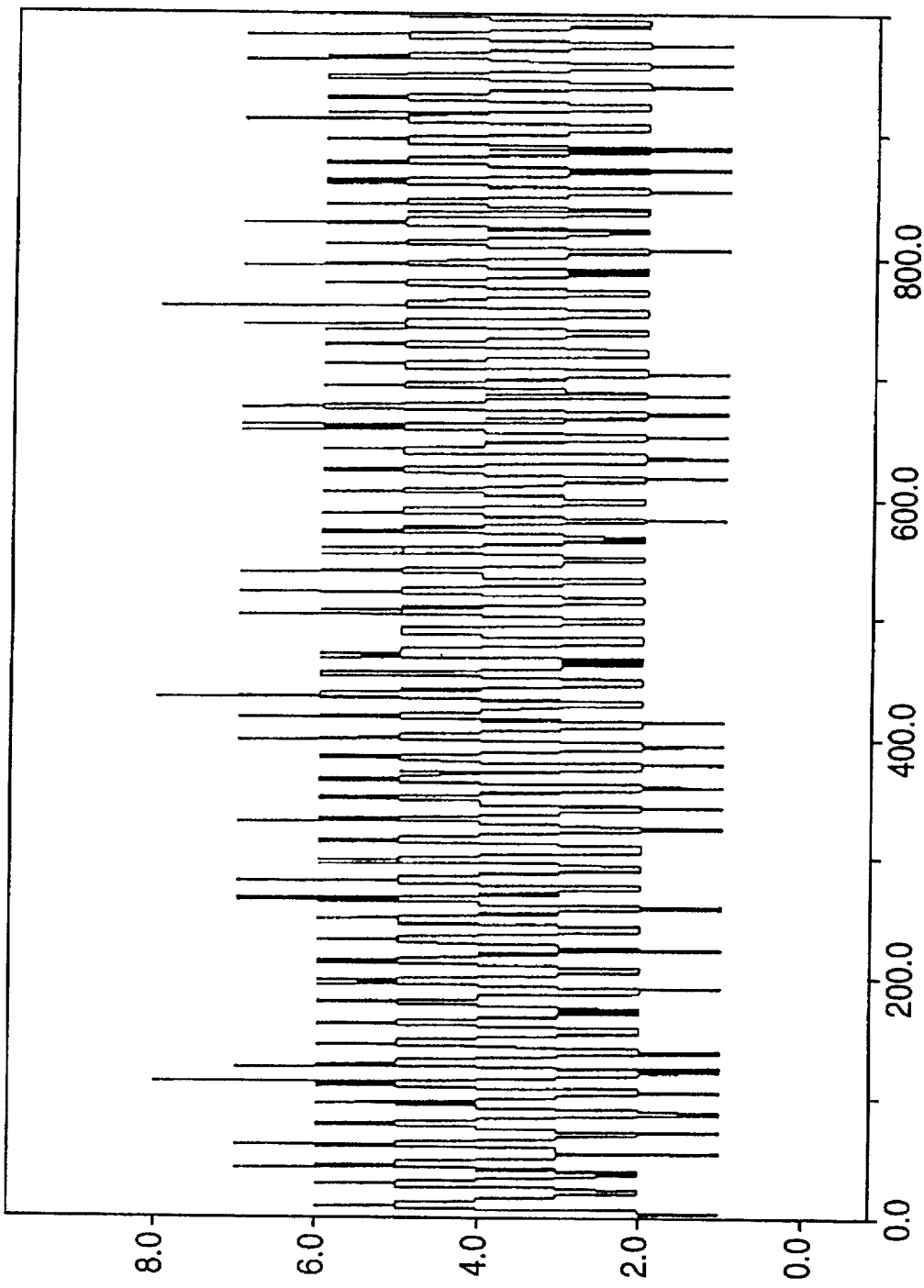
FIGS. 6–13 are graphs of output from photoreceivers or detectors as a function of the change in the electromagnetic radiation caused by passing through the material.
Figure 7:
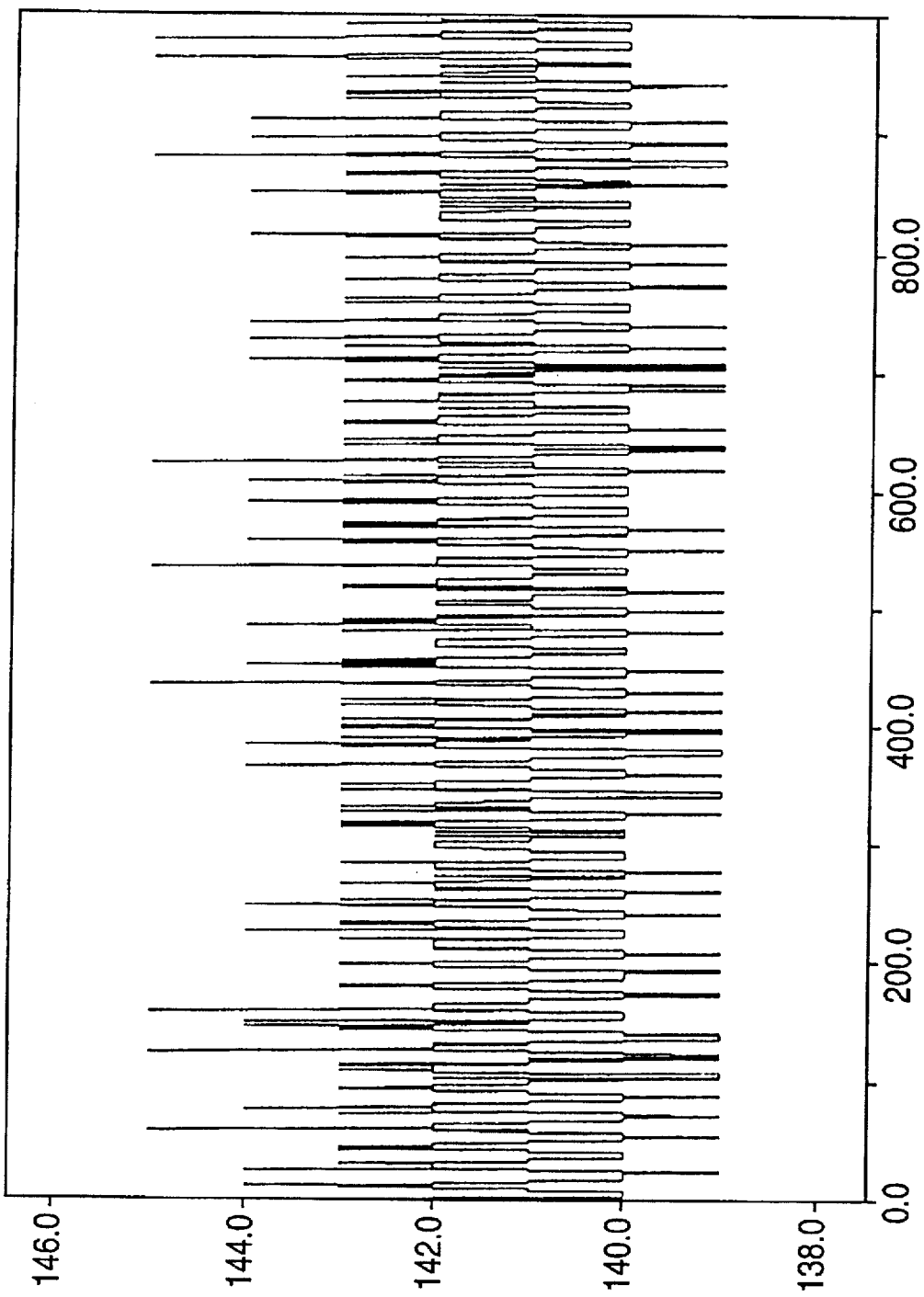
Figure 8:
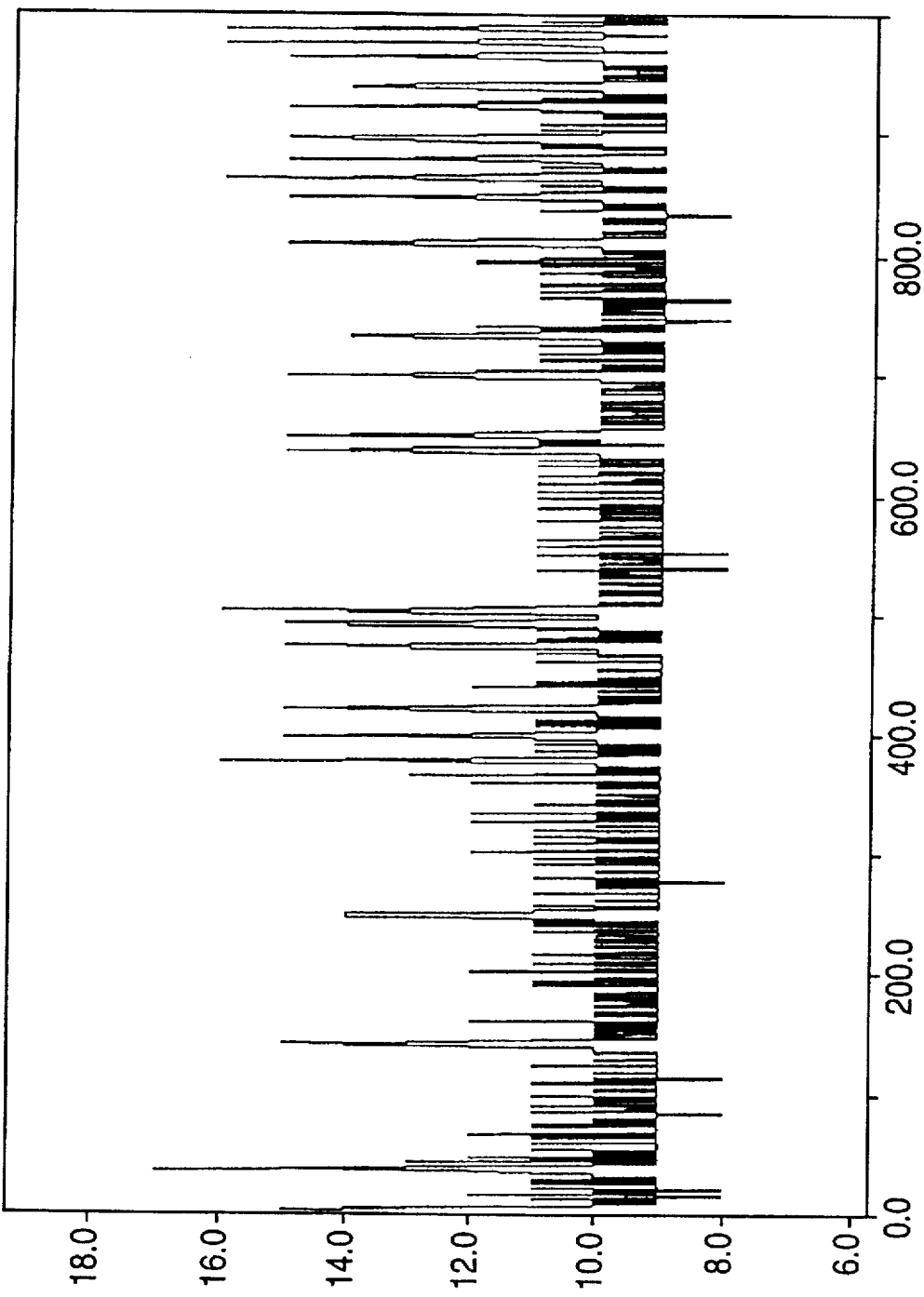
Figure 9:
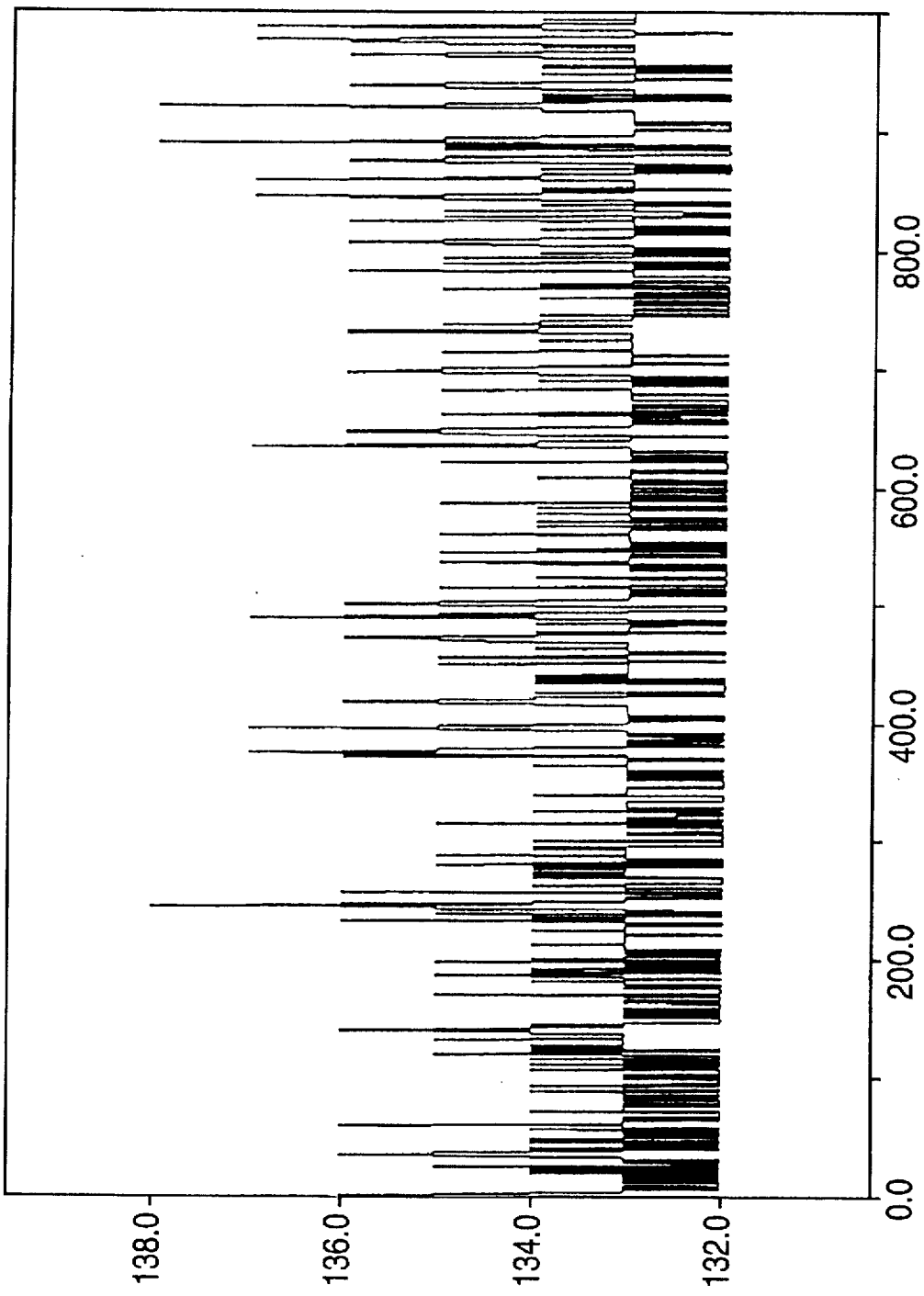
Figure 10:
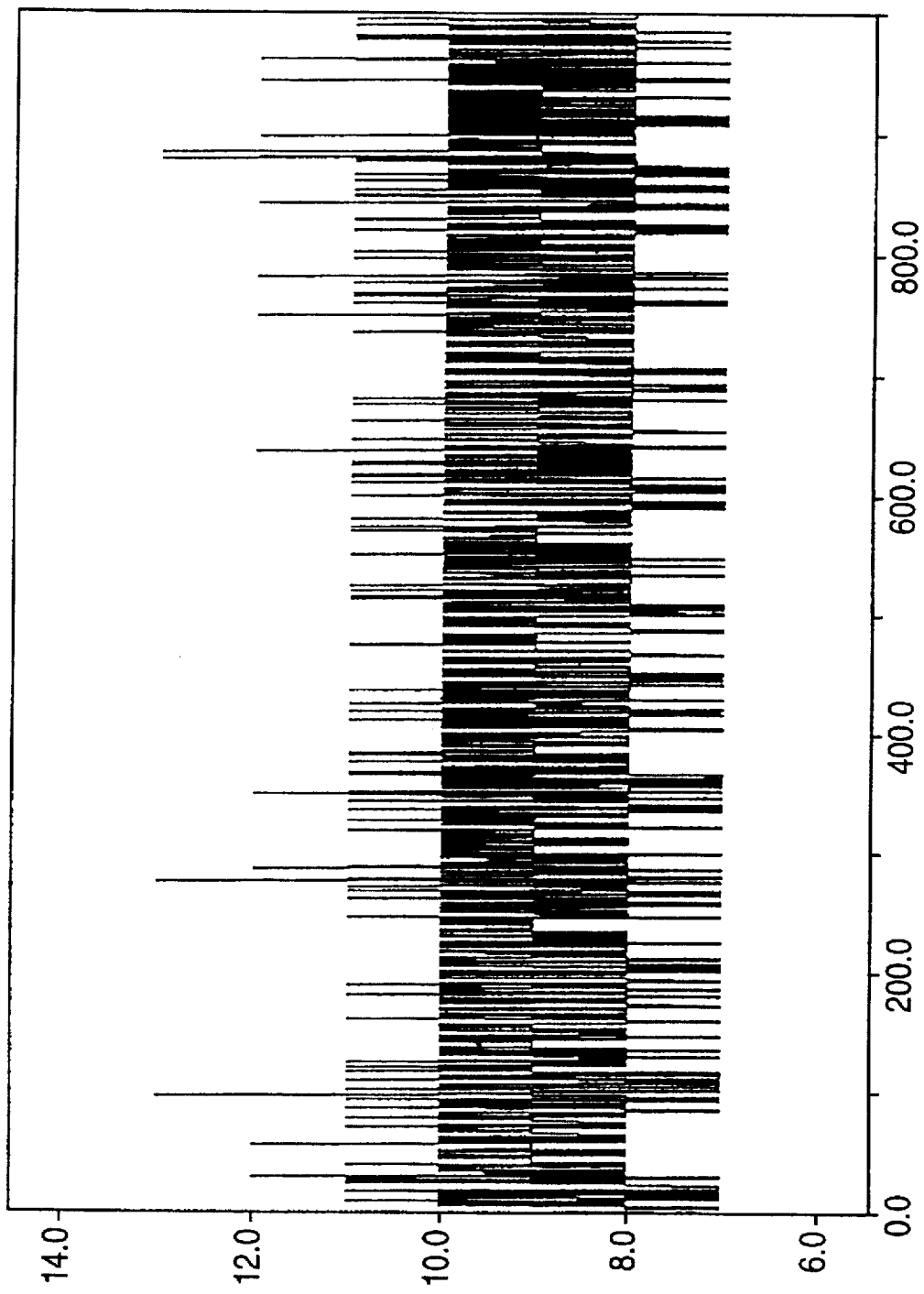
Figure 11:
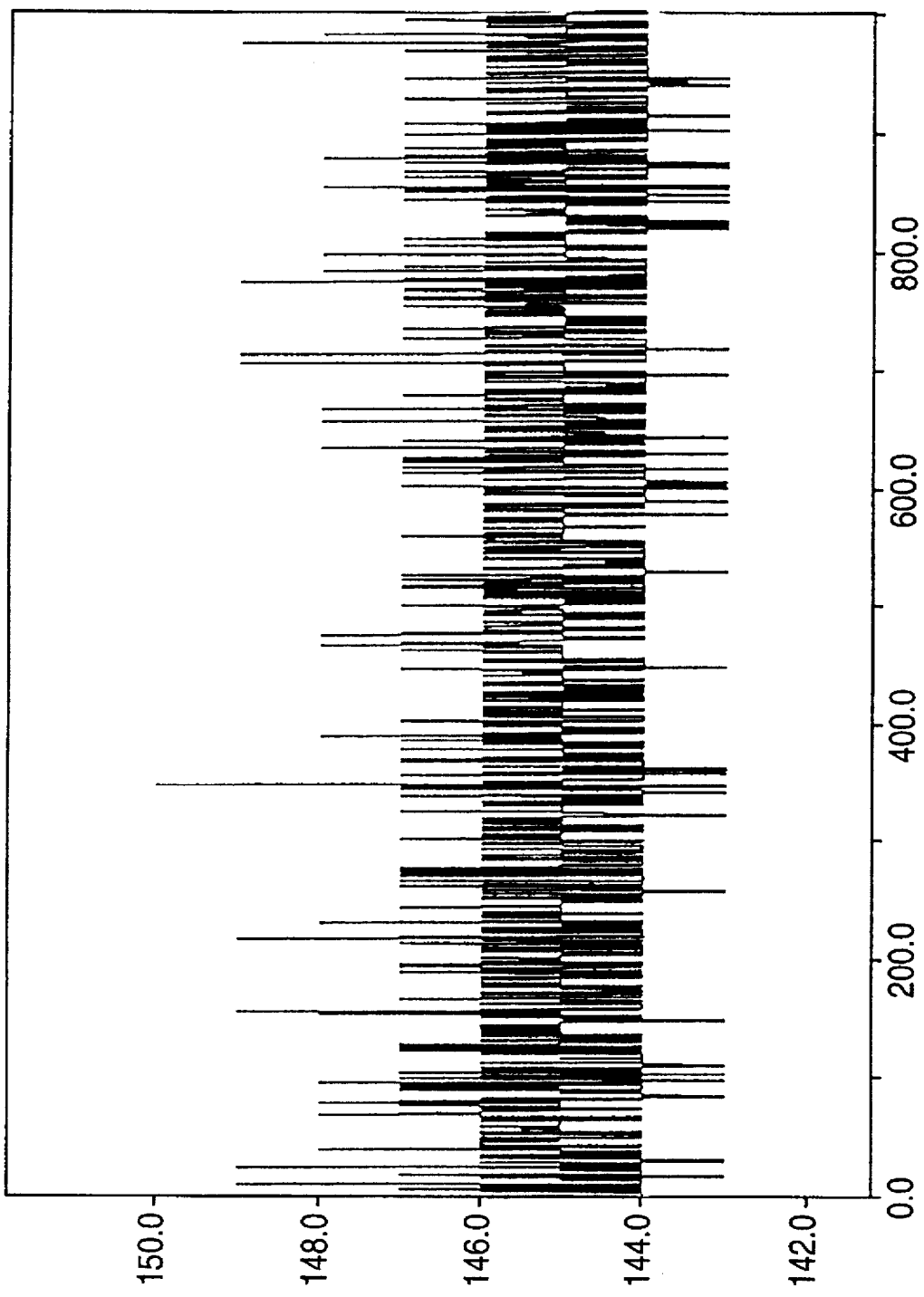
Figure 12:
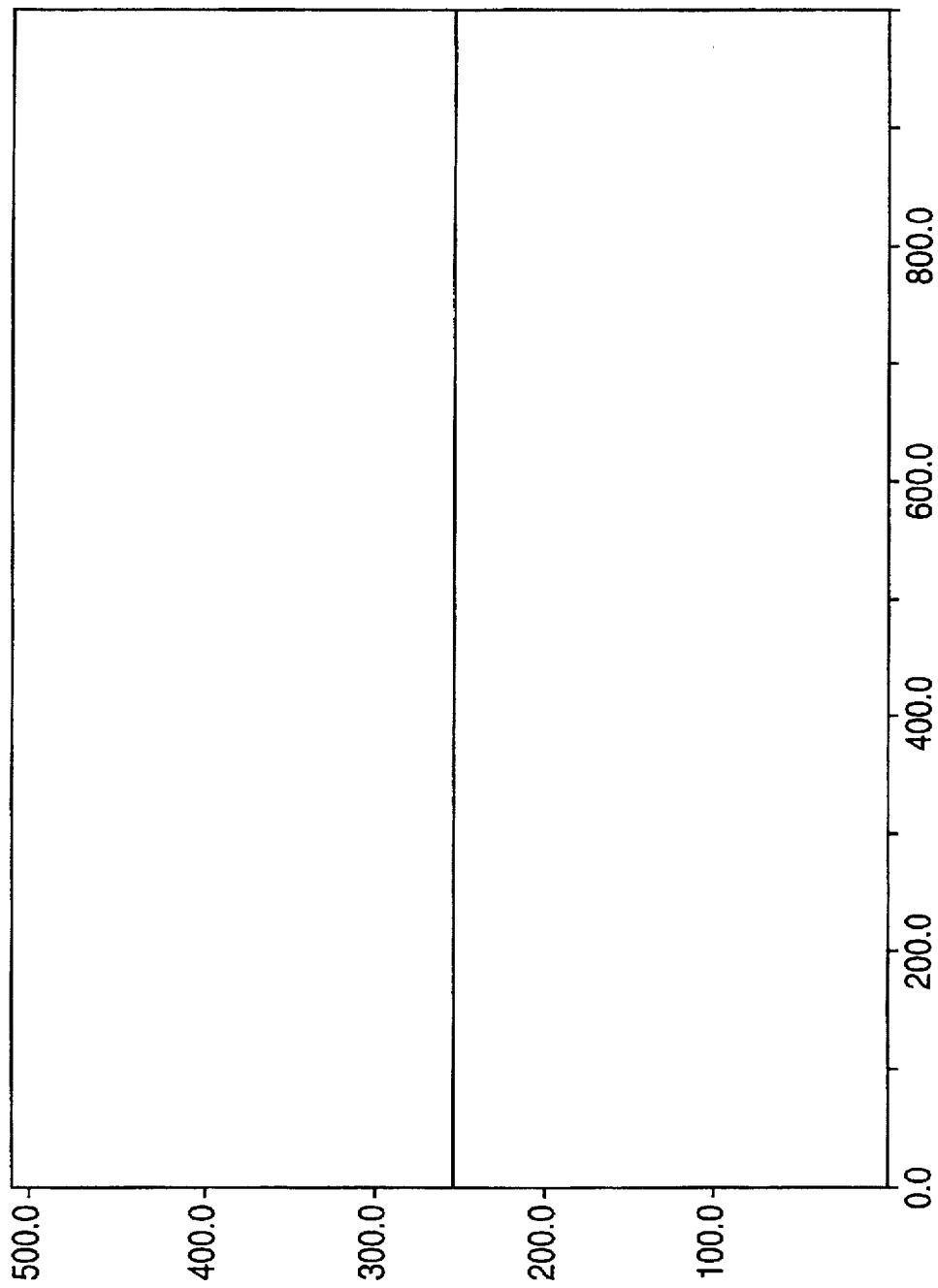
Figure 13:
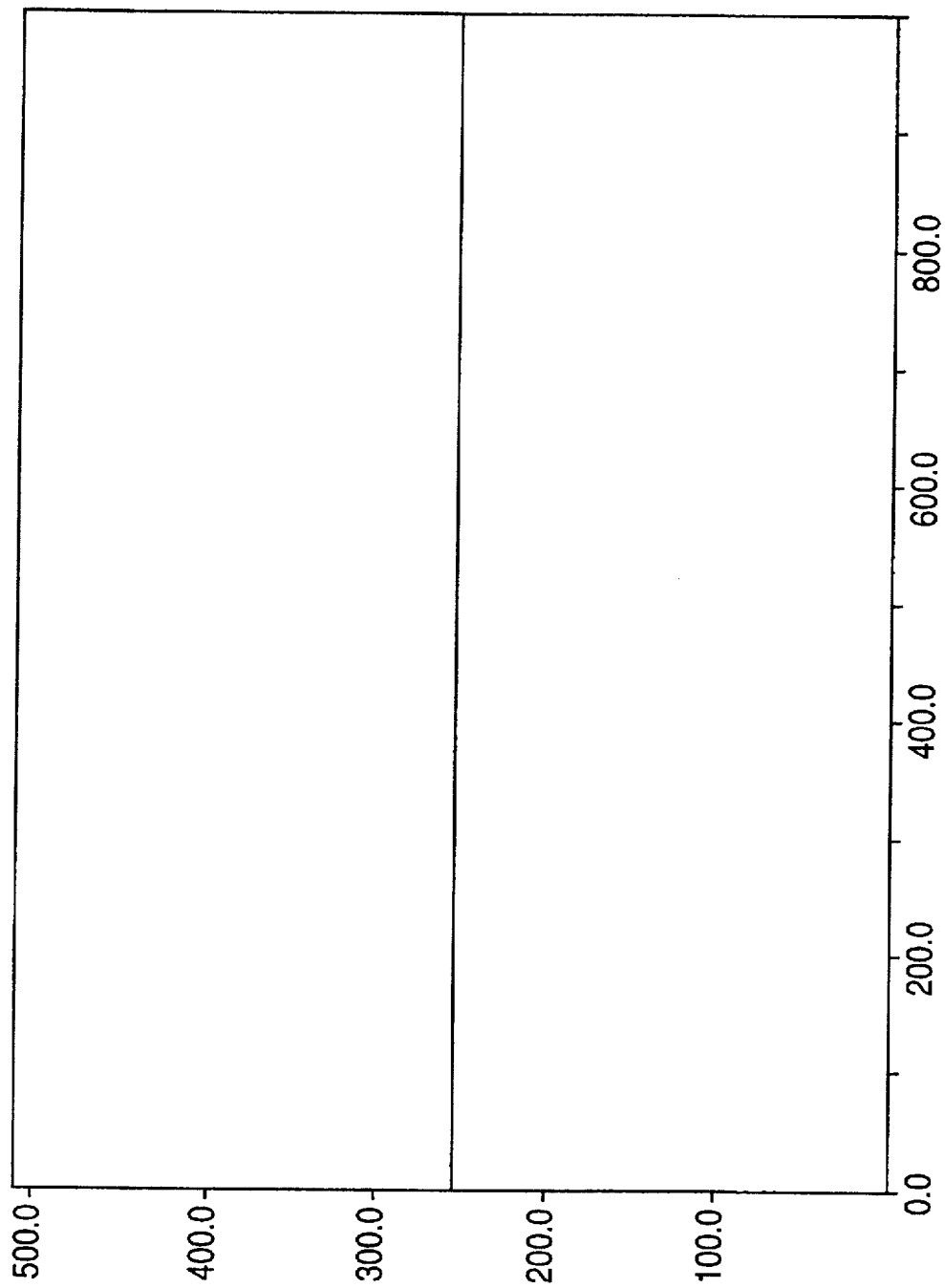

The features of the invention for determining a characteristic of a material described above can be understood more easily by a review of FIGS. 6–13, which graphs output from photoreceivers corresponding to characteristics of various materials with linear polarizers of first and second circular polarizers in parallel and crossed or perpendicular orientation to one another. As broadly embodied herein, FIGS. 6–13 depict the following information. FIG. 6 shows the raw data measured and graphed with the first and second circular polarizers parallel to each other with no container. FIG. 7 shows the raw data measured and graphed with the first and second circular polarizers crossed to each other with no container. FIG. 8 shows the raw data measured and graphed from changes to circularly polarized electromagnetic radiation having passed through clear vinyl with the first and second circular polarizers parallel to each other. FIG. 9 shows the raw data measured and graphed from changes to circularly polarized electromagnetic radiation having passed through clear vinyl with the first and second circular polarizers crossed to each other. FIG. 10 shows the raw data measured and graphed from changes to circularly polarized electromagnetic radiation having passed through clear glass with the first and second circular polarizer parallel to each other and no container. FIG. 11 shows the raw data measured and graphed from changes to circularly polarized electromagnetic radiation having passed through clear glass with the first and second circular polarizer crossed to each other. FIG. 12 shows raw data measured and graphed from changes to circularly polarized electromagnetic radiation having passed through clear PET with the first and second circular polarizer parallel to each other. FIG. 13 shows the raw data measured and graphed from changes to circularly polarized electromagnetic radiation having passed through clear PET with the first and second circular polarizer crossed to each other.

The raw data graphed for a no container test state, vinyl, and glass with circular polarizers both parallel and crossed produce different raw data measurements for the crossed and parallel state. However, FIGS. 12 and 13 illustrate that clear PET has a unique characteristic which causes the color values for both the crossed and parallel configuration of circular polarizers to have the same straight line value at a particular intensity. PET amplifies the intensity of the electromagnetic radiation. Other materials such as polypropylene also cause the color values to have the same level in both the parallel and crossed state, however, polypropylene reduces the intensity value. The color of PET may be determined by the actual color sensor that does not have the second circular polarizer between the material and the detector. Additionally, the material may be determined by a series of measurements that clarify the type of material since a given material may produce different readings at different points of measurement of the material.

Preferably, processor 72 includes determining what frequencies are affected when a simultaneously emitted polychromatic light source, which is circularly polarized, passes through a material. The type of molecular change or molecular structure of the material may be determined through this analysis. The electronics included in the processor 72 determines the degree or degrees of rotation of the electromagnetic radiation for varying wavelengths.

The present invention actually determines how the molecular structure of a given material affects the circular polarization of light because of the way it affects the photons in the electromagnetic radiation itself. Essentially there is activity between the electrical field around the molecule and the electrical field associated with the photons comprising the electromagnetic radiation. Since photons can be directed by the electrical fields and the phase changed and orientation changed, a characteristic of the material may be determined based on the changes caused by the electromagnetic radiation passing through the material.

Processing becomes more complicated when determining a characteristic of a material having residual stress. For example, a residual stress in a material, such as a long chain polymer, develop polarization characteristics of its own unrelated to the specific material. The characteristics relate to the stress induced in the material. For a more specific example, a translucent piece of long chain polymer plastic may be bent back and forth numerous times. If stretched, the long chain polymer develops stretched chains and creates a new shape having tension built up within the chains. These changes affect how the electromagnetic radiation is affected by the material. Specifically, when a crushed plastic container is deposited into a reverse vending machine, it is more difficult to make an accurate reading.

Another example includes polystyrenes that are stamp formed having induced stresses. When processing circularly polarized electromagnetic radiation having passed through a polystyrene cup, bands of bright red, bright blue, clear, green, yellow, and orange are produced; all of these different wavelength bands are detected. Preferably, a neural network is used for the processor electronics. Processor 72 preferably is taught that when a known material is shaped a certain way it includes certain stress issues. The processor 72 preferably knows that a polystyrene cup has stresses that look a certain way and therefore filters out the various color schemes caused by certain bends in certain products.

As a container is passed through the directed electromagnetic radiation, if processor 72 detects radical changes associated with the material itself, the processor preferably is taught to simply throw out the data that is radically different. Processor 72 preferably is taught that the material was obviously under stress and depending on the material itself, the present invention could be couple with shape identification and determine that a given output is expected for a cup. Processor 72 therefore is able to determine that, based on the shape of polystyrene cup, certain color bands are expected.

However, blow-molded containers are developed using a heat process that does not build up the same degree of residual stress. The heat process simply stretches the molecules in a known and expected manner. The properties of the material are not significantly changed since stress has been relieved through the heat process during shaping.

Materials containing pigments create additional concerns. For example, if a pigment is added to a container that eliminates blue wavelengths from passing through the material, then the processor preferably is taught that because of the color of the material, that certain wavelengths will be missing. If the rest of the electromagnetic radiation passing through the material indicates a specific material, then the processor can then recorrelate it to account for the color as well.

Various configurations of reverse vending machines are well known, and therefore will not be discussed here in further detail. The assembly and method for determining a characteristic of a material of the present invention is suitable for use with a number of reverse vending machines, and can be modified as necessary for a particular configuration.

The various embodiments of the present invention described above also may be utilized within a conveyor system for sorting containers in bulk. An embodiment of the proposed conveyor system is illustrated in FIG. 12 and includes an area into which containers may be dumped in bulk, a means for singulating and conveying containers into a sensing area, a sensing area for determining the color and composition of the container, a means for rejecting undesired containers from the container stream, and a means for conveying acceptable containers to a storage container or to further processing stations.

The area into which the containers will be dumped preferably is a large hopper 116 having a strain mechanism 118 with a cleated conveyor 120 to transfer the containers 68 to the sensing and sorting area 122. Each container 68 is delivered to a stage 124 where the container 68 preferably is held for the container material and color identification to take place. The identified containers further will travel to a separating system 126 for delivery to storage bins 128. Separating according to the container material and color identification preferably is done by sweeping rejected items from the stream of containers and by air jetting the acceptable containers 68 into storage bins 128.

A method for determining a characteristic of a material according to the present invention comprises the steps of directing an electromagnetic radiation having a first amount of circular polarization toward the material and processing the electromagnetic radiation after passing through the material to determine the characteristic of the material based on a change in the electromagnetic radiation. Additionally, the method may further comprise the steps of receiving the electromagnetic radiation having passed through the material and having a second amount of circular polarization, and removing the first amount of circular polarization from the electromagnetic radiation having the second amount of circular polarization prior to the step of processing. The method further may include the electromagnetic radiation having the second amount of circular polarization having a selected direction of rotation and further comprises the step of reversing the direction of rotation of the electromagnetic radiation having the second amount of circular polarization prior to the step of removing. The step of reversing includes reflecting the electromagnetic radiation. Finally, the method further may comprise the step of producing an electromagnetic radiation having circular polarization prior to the step of directing. The step of producing includes radiating an electromagnetic radiation and circularly polarizing the electromagnetic radiation with the direction of rotation.

Other embodiments of the invention will be apparent to those skilled in the art from consideration of the specification and practice of the invention disclosed herein. It is intended that the specification be considered as exemplary only, with a true scope and spirit being indicated by the following claims.

We claim:

1. A method for determining a characteristic of a material, comprising the steps of:

directing an electromagnetic radiation having a first amount of circular polarization towards the material; and processing the electromagnetic radiation after passing through the material to determine the composition of the material based on a change in the electromagnetic radiation.

2. The method of claim 1, wherein the step of processing determines the color of the material.

3. A method for determining a characteristic of a material, comprising the steps of:

introducing the material to a radiating area contained in a reverse vending machine;

directing an electromagnetic radiation produced by a polychromatic light source simultaneously emitting multiple wavelengths and having a first amount of circular polarization towards the material; and analyzing the electromagnetic radiation after passing through the material to determine the characteristic of the material based on a change in the electromagnetic radiation using at least two different wavelengths of light emitted by the polychromatic light source.

4. A method for determining a characteristic of a material, comprising the steps of:

directing an electromagnetic radiation having a first amount of circular polarization towards the material;

receiving the electromagnetic radiation having passed through the material and having a second amount of circular polarization;

removing the first amount of circular polarization from the electromagnetic radiation having the second amount of circular polarization; and processing the electromagnetic radiation after passing through the material to determine the characteristic of the material based on a change in the electromagnetic radiation.

5. The method of claim 4, wherein the electromagnetic radiation having the second amount of circular polarization has a selected direction of rotation and further comprises the step of reversing the direction of rotation of the electromagnetic radiation having the second amount of circular polarization prior to the step of removing.

6. The method of claim 5, wherein the step of reversing includes reflecting the electromagnetic radiation.

7. The method of claim 4, further comprising the step of producing an electromagnetic radiation having circular polarization prior to the step of directing.

8. The method of claim 7, wherein the step of producing includes radiating an electromagnetic radiation and circularly polarizing the electromagnetic radiation with a direction of rotation.

9. The method of claim 7, wherein the step of producing includes illuminating with a polychromatic light source.

10. The method of claim 8, wherein the step of producing includes passing the electromagnetic radiation from the light source through a first circular polarizing filter in a first direction.

11. The method of claim 10, wherein the step of removing includes passing the electromagnetic radiation through a second circular polarizing filter.

12. The method of claim 11, wherein the first and second circular polarizing filters include a linear polarizer having a phase orientation and a quarter wave retarder.

13. The method of claim 10, wherein the step of removing includes passing the electromagnetic radiation through the first circular polarizing filter in a second direction opposite the first direction.

14. The method of claim 12, wherein the linear polarizer of the second circular polarizing filter is oriented 90 degrees out of phase with that of the first circular polarizing filter.

* * * * *